United States Patent
Ohta et al.

(10) Patent No.: US 9,870,894 B2
(45) Date of Patent: Jan. 16, 2018

(54) EMBEDDING RESIN COMPOSITION FOR ELECTRON MICROSCOPEY AND METHOD FOR OBSERVING SAMPLE WITH ELECTRON MICROSCOPE USING THE SAME

(75) Inventors: Keisuke Ohta, Fukuoka (JP); Toshiyuki Kiryu, Gunma (JP)

(73) Assignee: KURUME UNIVERSITY, Fukuoka (JP)

( * ) Notice: Subject to any disclaimer, the term of this patent is extended or adjusted under 35 U.S.C. 154(b) by 116 days.

(21) Appl. No.: 14/342,460

(22) PCT Filed: Sep. 4, 2012

(86) PCT No.: PCT/JP2012/072418
§ 371 (c)(1),
(2), (4) Date: Apr. 16, 2014

(87) PCT Pub. No.: WO2013/035681
PCT Pub. Date: Mar. 14, 2013

(65) Prior Publication Data
US 2014/0212913 A1   Jul. 31, 2014

(30) Foreign Application Priority Data

Sep. 6, 2011 (JP) ................... 2011-193828
Nov. 11, 2011 (JP) ................... 2011-247267
Nov. 29, 2011 (JP) ................... 2011-259674

(51) Int. Cl.
| | | |
|---|---|---|
| H01J 37/26 | (2006.01) |
| G01N 23/00 | (2006.01) |
| C09D 163/00 | (2006.01) |
| G01N 1/36 | (2006.01) |
| C08L 63/00 | (2006.01) |
| G01N 23/225 | (2006.01) |

(52) U.S. Cl.
CPC .............. *H01J 37/26* (2013.01); *C08L 63/00* (2013.01); *C09D 163/00* (2013.01); *G01N 1/36* (2013.01); *G01N 23/00* (2013.01); *G01N 23/225* (2013.01)

(58) Field of Classification Search
CPC ........ H01J 37/26; C08L 63/00; C09D 163/00; G01N 1/28; G01N 1/36; G01N 23/00; G01N 23/225; G01N 1/30
USPC .......................................................... 435/29
See application file for complete search history.

(56) References Cited
U.S. PATENT DOCUMENTS
2009/0173882 A1   7/2009  Kuwabata et al.

FOREIGN PATENT DOCUMENTS

| | | |
|---|---|---|
| EP | 1693430 A2 | 8/2006 |
| JP | 58-161845 | 9/1983 |
| JP | 2-069635 | 3/1990 |
| JP | H03-122165 A | 5/1991 |
| JP | H0526794 A | 2/1993 |
| JP | 8-306235 | 11/1996 |
| JP | 11-030575 | 2/1999 |
| JP | H11-153522 A | 6/1999 |
| JP | 2010256095 A | 11/2010 |
| JP | 2011060555 A | 3/2011 |
| JP | 2011117826 A | 6/2011 |
| JP | 2011137807 A | 7/2011 |
| WO | WO-2007083756 A1 | 7/2007 |
| WO | WO-2010037918 A1 | 4/2010 |
| WO | WO-2010084938 A1 | 7/2010 |

OTHER PUBLICATIONS

Matsumoto et al. (2008). Confinement of Ionic Liquid by Networked Polymers Based on Multifunctional Epoxy Resins. Macromolecules, v41, p. 6981-6986.*
Plechkova et al. (2008). Applications of ionic liquids in the chemical industry. Chem. Soc. Rev., v37, p. 123-150.*

(Continued)

*Primary Examiner* — Sean C. Barron
(74) *Attorney, Agent, or Firm* — Marshall, Gerstein & Borun LLP

(57) ABSTRACT

The present invention provides an embedding resin composition for electron microscopy having satisfactory performance as an embedding medium, including embedding performance and sectioning quality, and exhibiting excellent antistatic performance; and a method for observing a sample with an electron microscope using the composition. The embedding resin composition for electron microscopy of the present invention having antistatic performance comprises an ionic liquid and an embedding medium comprising an epoxy-based resin, a methacrylate resin or an unsaturated polyester resin. Preferably, the ionic liquid comprising a quaternary ammonium compound based on the formula (I):

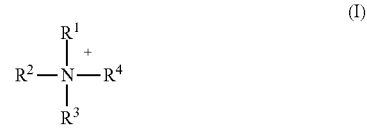

and an anion selected from the group consisting of $BF_4^-$, $PF_6^-$, $(CF_3SO_2)_2N^-$, a halide ion, a conjugate base of carboxylic acid, a conjugate base of sulfonic acid and a conjugate base of an inorganic acid.

11 Claims, 11 Drawing Sheets

(56) References Cited

OTHER PUBLICATIONS

Sanes et al. Effect of the addition of room temperature ionic liquid and ZnO nanoparticles on the wear and scratch resistance of epoxy resin. Wear (2010), v268, p. 1295-1302.*
Tanaka et al. Freezed Resin Cracking Method for Scanning Electron Microscopy of Biological Materials. Naturwissenschaften (1972), v59(2), p. 77-77.*
Extended European Search Report in corresponding PCT/JP2012/072418 dated Apr. 15, 2015.
International Search Report in corresponding PCT/JP2012/072418 dated Oct. 2, 2012.
Written Opinion in corresponding PCT/JP2012/072418 dated Oct. 2, 2012.
International Preliminary Report on Patentability in corresponding PCT/JP2012/072418 dated Feb. 7, 2013.

* cited by examiner

EMBEDDING RESIN COMPOSITION FOR ELECTRON MICROSCOPEY AND METHOD FOR OBSERVING SAMPLE WITH ELECTRON MICROSCOPE USING THE SAME

TECHNICAL FIELD

The present invention relates to an embedding resin composition for electron microscopy and a method for observing a sample with an electron microscope using the composition.

BACKGROUND ART

Electron microscopes are generally used to investigate the ultrastructure of biological samples such as cells and tissue, polymer resin samples, and crystalline samples such as inorganic substances. Two types of electron microscopes are known, including scanning electron microscopes (hereinafter sometimes referred to as SEMs) and transmission electron microscopes (hereinafter sometimes referred to as TEMs).

Patent Literature 1 describes a sample preparation method in which a sample to be observed is embedded in an embedding medium and thin sectioned with a microtome etc. The embedding medium used is an epoxy resin, an unsaturated polyester resin, an acrylic resin, or the like, all of which are insulating materials. Consequently, the resin tends to charge at the time of observation with an electron microscope and this may cause difficulty in examining the subject. In some cases such charging may result in discharge phenomena inside the electron microscope, which may damage the detectors. These problems become obstacles especially when insulating materials are observed with a SEM.

In order to overcome the problems relating to charging during observation with a SEM, various modifications of observation technique have been conventionally introduced. For example, observation with a SEM has been conventionally carried out under conditions in which incident electrons and emitted electrons are in a particular angle relationship, or under low-vacuum conditions, or under low-current conditions. However, these modifications have drawbacks. For example, the observation range is narrow, contrast and resolution are insufficient, and elemental analysis cannot be conducted.

Patent Literature 2 discloses an epoxy resin composition having antistatic performance, produced by adding an alkali metal salt and a polyether-based polymer to an epoxy resin. However, the composition lacks sufficient mechanical strength and therefore does not provide satisfactory performance as an embedding medium, including embedding performance and sectioning quality.

CITATION LIST

Patent Literature

Patent Literature 1: JP 5-26794 A
Patent Literature 2: JP 3-122165 A

SUMMARY OF INVENTION

Technical Problem

The present invention was developed in view of the above problems in the conventional art. An object of the present invention is to provide an embedding resin composition for electron microscopy having satisfactory performance as an embedding medium, including embedding performance and sectioning quality, and exhibiting excellent antistatic performance; and to provide a method for observing a sample with an electron microscope using the composition.

Solution to Problem

To solve the above problems, the present invention includes the following.

[1] An embedding resin composition for electron microscopy, the composition having antistatic performance and comprising an ionic liquid and an embedding medium comprising an epoxy-based resin, a methacrylate resin or an unsaturated polyester resin.

[2] The composition according to the above [1], wherein the ionic liquid comprising
a quaternary ammonium compound based on the formula (I):

(in the formula (I), $R^1$, $R^2$, $R^3$ and $R^4$ are independently a hydrogen atom, an alkyl group, an alkynyl group, an alkenyl group, an alkadiene group, an alkatriene group, a cycloalkyl group or an aliphatic heterocyclic group and any of the hydrogen atoms of the groups may be replaced with a substituent; at least one of $R^1$, $R^2$, $R^3$ and $R^4$ contains an alkenyl group, an alkadiene group, an alkatriene group or an epoxy group; and $R^1$, $R^2$, $R^3$ and $R^4$ may bind to each other to form a ring) and
an anion selected from the group consisting of $BF_4^-$, $PF_6^-$, $(CF_3SO_2)_2N^-$, a halide ion, a conjugate base of carboxylic acid, a conjugate base of sulfonic acid and a conjugate base of an inorganic acid.

[3] The composition according to the above [2], wherein $R^1$ is an epoxy group, a glycidyl group, or an alkenyl group of 2 to 10 carbon atoms.

[4] The composition according to the above [2] or [3], wherein $R^2$, $R^3$ and $R^4$ are independently an alkyl group of 1 to 6 carbon atoms.

[5] The composition according to any of the above [2] to [4], wherein the quaternary ammonium compound is a monomer, an oligomer or a mixture thereof.

[6] The composition according to any of the above [2] to [5], wherein the anion is $(CF_3SO_2)_2N^-$.

[7] The composition according to any of the above [1] to [6], wherein the amount of the ionic liquid is 5 to 35 vol % relative to the total volume of the composition.

[8] A method for observing a sample with an electron microscope, the method comprising the step of embedding a sample in the composition according to any of the above [1] to [7].

[9] The observation method according to the above [8], wherein the method comprises the step of staining a sample and the staining step is performed before the embedding step.

[10] The observation method according to the above [8] or [9], wherein the electron microscope is a scanning electron microscope.

[11] The observation method according to any of the above [8] to [10], wherein the sample is a biological sample.

[12] The observation method according to the above [11], wherein the biological sample is a cell or tissue of a plant or animal.

[13] The observation method according to any of the above [8] to [10], wherein the sample is a non-biological sample.

[14] The observation method according to the above [13], wherein the non-biological sample is a resin, a rubber, a synthetic resin, a pigment, a coating material, a cosmetic, a pharmaceutical drug, a ceramic, a magnetic body, a magnetic material, a semiconductor, a metal, a metal oxide, a mineral, an organic salt, or an inorganic salt.

[15] The observation method according to any of the above [8] to [14], wherein the sample is a powder.

Advantageous Effects of Invention

The embedding resin composition for electron microscopy of the present invention has satisfactory performance as an embedding medium, including embedding performance and sectioning quality, and exhibits excellent antistatic performance.

DESCRIPTION OF EMBODIMENTS

Figure 1:
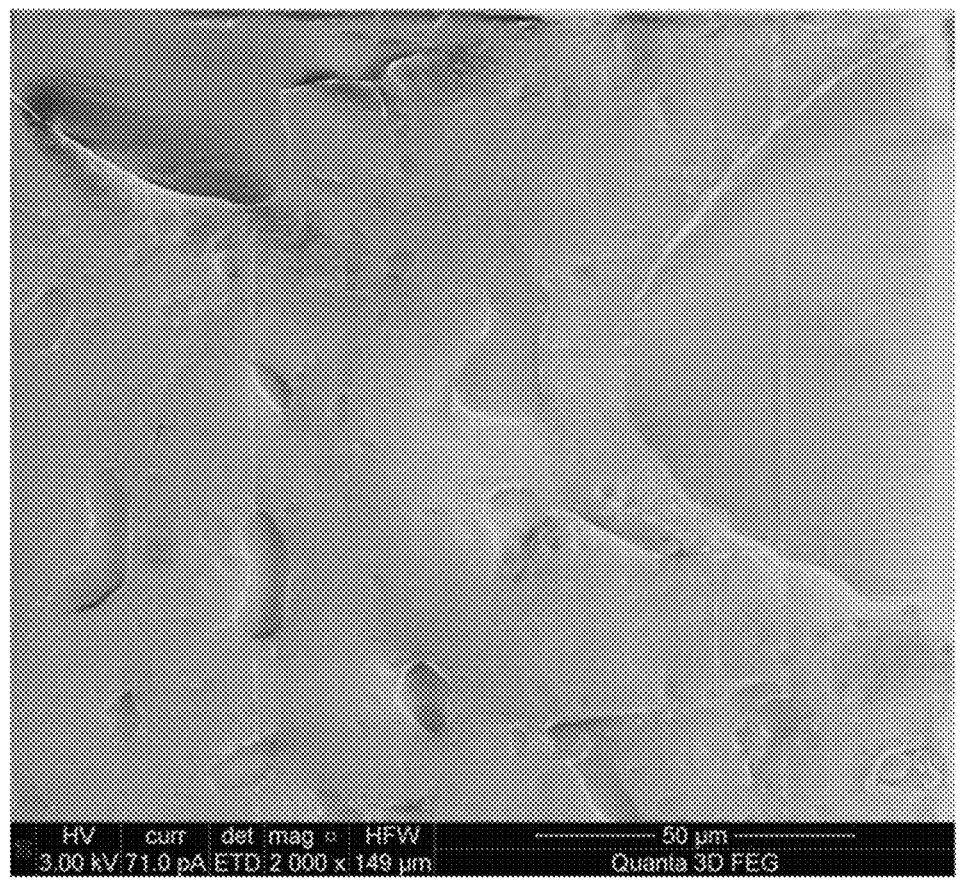
FIG. 1 is a photograph showing the results of electron microscope observation of hepatocytes embedded in the embedding resin composition for electron microscopy of Example 1 (2000-fold magnification).

The embedding resin composition for electron microscopy of the present invention has antistatic performance and comprises an ionic liquid and an embedding medium comprising an epoxy-based resin, a methacrylate resin or an unsaturated polyester resin.

Ionic Liquid

The ionic liquid used in the present invention refers to a salt which is in the liquid state at normal temperature.

Cation

The cation of the ionic liquid of the present invention is not particularly limited as long as it constitutes the ionic liquid. The cation may be, for example, imidazolium, pyridium, pyrrolidinium, quaternary phosphonium, quaternary ammonium, or the like. The cation may be one kind or a mixture of two or more kinds.

Examples of the imidazolium include 1,3-dimethylimidazolium, 1-ethyl-3-methylimidazolium, 1-ethyl-3-methylimidazolium, 1-methyl-3-propylimidazolium, 1-butyl-3-methylimidazolium, 1-hexyl-3-methylimidazolium, 1-butyl-2,3-dimethylimidazolium, etc.

Examples of the pyridinium include 1-ethylpyridinium, 1-butylpyridinium, 1-butyl-4-methylpyridinium, 1-ethyl-3-methylpyridinium, 1-ethyl-3-(hydroxymethyl)pyridinium, etc.

Examples of the pyrrolidinium include N-methyl-N-propylpyrrolidinium, N-methyl-N-butylpyrrolidinium, etc.

Examples of the quaternary phosphonium include tributyllaurylphosphonium, tributylmyristylphosphonium, tributylcetylphosphonium, tributylstearylphosphonium, triphenyllaurylphosphonium, triphenylmyristylphosphonium, triphenylcetylphosphonium, triphenylstearylphosphonium, benzyldimethyllaurylphosphonium, benzyldimethylmyristylphosphonium, benzyldimethylcetylphosphonium, benzyldimethylstearylphosphonium, etc.

Examples of the quaternary ammonium include tetraalkylammonium such as tetramethylammonium, tetraethylammonium, and triethylmethylammonium; triazolium, pyridazinium, thiazolium, oxazolium, pyrimidinium, pyrazinium, etc.

Preferably, the cation of the ionic liquid used in the present invention is quaternary ammonium. More preferably, the ionic liquid comprises, as a cation, a quaternary ammonium compound based on the following formula (I):

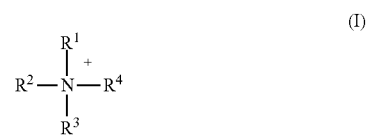

(in the formula (I), $R^1$, $R^2$, $R^3$ and $R^4$ are independently a hydrogen atom, an alkyl group, an alkynyl group, an alkenyl group, an alkadiene group, an alkatriene group, a cycloalkyl group or an aliphatic heterocyclic group and any of the hydrogen atoms of the groups may be replaced with a substituent; at least one of $R^1$, $R^2$, $R^3$ and $R^4$ contains an alkenyl group, an alkadiene group, an alkatriene group or an epoxy group; and $R^1$, $R^2$, $R^3$ and $R^4$ may bind to each other to form a ring).

The alkyl group represented by $R^1$, $R^2$, $R^3$ and/or $R^4$ may be linear or branched and examples thereof include a linear or branched alkyl group of 1 to 20 carbon atoms. Specific examples thereof include a linear or branched alkyl group such as methyl, ethyl, n-propyl, isopropyl, n-butyl, sec-butyl, isobutyl, tert-butyl, n-pentyl, neopentyl, tert-pentyl, isopentyl, 2-methylbutyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, heptyl, octyl, nonyl, decyl, cetyl, stearyl, etc. Preferably, the alkyl group is of 1 to 12 carbon atoms, more preferably 1 to 6 carbon atoms.

The alkynyl group represented by $R^1$, $R^2$, $R^3$ and/or $R^4$ may be linear or branched and examples thereof include an alkynyl group of 2 to 15 carbon atoms, preferably 2 to 10 carbon atoms, more preferably 2 to 6 carbon atoms. Specific examples thereof include ethynyl, 1-propynyl, 2-propynyl, 1-butynyl, 3-butynyl, pentynyl, hexynyl, etc.

The alkenyl group represented by $R^1$, $R^2$, $R^3$ and/or $R^4$ may be linear or branched and examples thereof include an alkenyl group of 2 to 15 carbon atoms, preferably 2 to 10 carbon atoms, more preferably 2 to 6 carbon atoms. Specific examples thereof include vinyl, 1-propenyl, allyl, 1-butenyl, 2-butenyl, 3-butenyl, pentenyl, hexenyl, isopropenyl, 2-methyl-2-propenyl, 1-methyl-2-propenyl, 2-methyl-1-propenyl, etc.

The alkadiene group represented by $R^1$, $R^2$, $R^3$ and/or $R^4$ may be linear or branched and examples thereof include an alkadiene group of 3 to 15 carbon atoms, preferably 4 to 10 carbon atoms. Specific examples thereof include butadiene, pentadiene, hexadiene, etc.

The alkatriene group represented by $R^1$, $R^2$, $R^3$ and/or $R^4$ may be linear or branched and examples thereof include an alkatriene group of 4 to 15 carbon atoms, preferably 6 to 12 carbon atoms. Specific examples thereof include hexatriene, heptatriene, octatriene, etc.

The cycloalkyl group represented by $R^1$, $R^2$, $R^3$ and/or $R^4$ is, for example, a cycloalkyl group of 3 to 14 carbon atoms, preferably 5 to 12 carbon atoms, more preferably 6 to 12 carbon atoms. Specific examples thereof include cyclopropyl, cyclobutyl, cyclopentyl, methylcyclopentyl, cyclohexyl, cycloheptyl, cyclooctyl, 1,2-dimethylcyclopentyl, 1,3-dimethylcyclopentyl, 1-ethyl-2-methylcyclopentyl, etc.

The aliphatic heterocyclic group represented by $R^1$, $R^2$, $R^3$ and/or $R^4$ is, for example, a 5- to 8-membered, preferably 5- or 6-membered, monocyclic aliphatic heterocyclic group or a polycyclic or fused aliphatic heterocyclic group, the group having 2 to 14 carbon atoms and containing at least one heteroatom, preferably 1 to 3 heteroatoms, such as a nitrogen atom, an oxygen atom and a sulfur atom. Examples of the aliphatic heterocyclic group include pyrrolidyl-2-one, piperidino, piperazinyl, morpholino, tetrahydrofuryl, tetrahydropyranyl, tetrahydrothienyl, etc.

Any of the hydrogen atoms of the alkyl group, the alkynyl group, the alkenyl group, the alkadiene group, the alkatriene group, the cycloalkyl group or the aliphatic heterocyclic group represented by $R^1$, $R^2$, $R^3$ and/or $R^4$ may be replaced with a substituent. The substituent is not particularly limited and examples thereof include alkyl, alkynyl, alkenyl, alkadiene, alkatriene, aryl, alkoxy, alkylenedioxy, aryloxy, aralkyloxy, heteroaryloxy, alkylthio, cycloalkyl, aliphatic heterocyclic, arylthio, aralkylthio, heteroarylthio, amino, substituted amino, cyano, hydroxyl, oxo, epoxy, glycidyl, nitro, and mercapto groups, a halogen atom, etc. The number of the substituents is preferably 1 to 3, more preferably 1 or 2.

The alkyl group as the substituent may be linear or branched and examples thereof include a linear or branched alkyl group of 1 to 20 carbon atoms. Specific examples thereof are the same as those listed for the above alkyl group represented by $R^1$, $R^2$, $R^3$ and/or $R^4$.

The alkynyl group as the substituent may be linear or branched and examples thereof include an alkynyl group of 2 to carbon atoms, preferably 2 to 10 carbon atoms, more preferably 2 to 6 carbon atoms. Specific examples thereof are the same as those listed for the above alkynyl group represented by $R^1$, $R^2$, $R^3$ and/or $R^4$.

The alkenyl group as the substituent may be linear or branched and examples thereof include an alkenyl group of 2 to carbon atoms, preferably 2 to 10 carbon atoms, more preferably 2 to 6 carbon atoms. Specific examples thereof are the same as those listed for the above alkenyl group represented by $R^1$, $R^2$, $R^3$ and/or $R^4$.

The alkadiene group as the substituent may be linear or branched and examples thereof include an alkadiene group of 3 to 15 carbon atoms, preferably 4 to 10 carbon atoms. Specific examples thereof are the same as those listed for the above alkadiene group represented by $R^1$, $R^2$, $R^3$ and/or $R^4$.

The alkatriene group as the substituent may be linear or branched and examples thereof include an alkatriene group of 4 to 15 carbon atoms, preferably 6 to 12 carbon atoms. Specific examples thereof are the same as those listed for the above alkatriene group represented by $R^1$, $R^2$, $R^3$ and/or $R^4$.

The cycloalkyl group as the substituent is, for example, a cycloalkyl group of 3 to 14 carbon atoms, preferably 5 to 12 carbon atoms, more preferably 6 to 12 carbon atoms. Specific examples thereof are the same as those listed for the above cycloalkyl group represented by $R^1$, $R^2$, $R^3$ and/or $R^4$.

The aliphatic heterocyclic group as the substituent is, for example, a 5- to 8-membered, preferably 5- or 6-membered, monocyclic aliphatic heterocyclic group or a polycyclic or fused aliphatic heterocyclic group, the group having 2 to 14 carbon atoms and containing at least one heteroatom, preferably 1 to 3 heteroatoms, such as a nitrogen atom, an oxygen atom and a sulfur atom. Specific examples thereof are the same as those listed for the above aliphatic heterocyclic group represented by $R^1$, $R^2$, $R^3$ and/or $R^4$.

Examples of the aryl group as the substituent include an aryl group of 6 to 20 carbon atoms and specific examples thereof include phenyl, 1-naphthyl, 2-naphthyl, anthryl, phenanthryl, 2-biphenyl, 3-biphenyl, 4-biphenyl, terphenyl, etc.

Examples of the aryloxy group as the substituent include an aryloxy group of 6 to 14 carbon atoms and specific examples thereof include phenoxy, tolyloxy, xylyloxy, naphthoxy, anthryloxy, etc.

Examples of the aralkyl group as the substituent include a group derived from the above alkyl group by replacing at least one hydrogen atom with the above aryl group and example thereof include an aralkyl group of 7 to 18 carbon atoms. Specific examples thereof include benzyl, phenethyl, 1-phenylpropyl, 3-naphthylpropyl, diphenylmethyl, 1-naphthylmethyl, 2-naphthylmethyl, 2,2-diphenylethyl, 3-phenylpropyl, 4-phenylbutyl, 5-phenylpentyl, etc.

Examples of the aromatic heterocyclic group as the substituent include a 5- to 8-membered, preferably 5- or 6-membered, monocyclic heteroaryl group or a polycyclic or fused heteroaryl group, the group having 2 to 15 carbon atoms and containing at least one heteroatom, preferably 1 to 3 heteroatoms, such as a nitrogen atom, an oxygen atom and a sulfur atom. Examples of the 5- or 6-membered monocyclic heteroaryl group and the polycyclic or fused heteroaryl group include furyl, thienyl, pyrrolyl, pyridyl, pyrimidyl, pyrazyl, pyridazyl, pyrazolyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzimidazolyl, benzoxazolyl, benzothiazolyl, etc.

The alkoxy group as the substituent may be linear, branched or cyclic and examples thereof include an alkoxy group of 1 to 6 carbon atoms. Specific examples thereof include methoxy, ethoxy, n-propoxy, isopropoxy, n-butoxy, sec-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, methoxymethoxy, 2-ethoxyethoxy, etc.

Examples of the alkylenedioxy group as the substituent include an alkylenedioxy group of 1 to 3 carbon atoms. Specific examples thereof include methylenedioxy, ethylenedioxy, trimethylenedioxy, propylenedioxy, isopropylidenedioxy, etc.

The alkylthio group as the substituent may be linear, branched or cyclic and examples thereof include an alkylthio group of 1 to 6 carbon atoms. Specific examples thereof include methylthio, ethylthio, n-propylthio, isopropylthio, n-butylthio, 2-butylthio, isobutylthio, tert-butylthio, pentylthio, hexylthio, cyclohexylthio, etc.

Examples of the aralkyloxy group as the substituent include an aralkyloxy group of 7 to 12 carbon atoms and specific examples thereof include benzyloxy, 1-phenylethoxy, 2-phenylethoxy, 1-phenylpropoxy, 2-phenylpropoxy, 3-phenylpropoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy, 6-phenylhexyloxy, etc.

Examples of the arylthio group as the substituent include an arylthio group of 6 to 14 carbon atoms and specific examples thereof include phenylthio, tolylthio, xylylthio, naphthylthio, etc.

Examples of the heteroaryloxy group as the substituent include a heteroaryloxy group having 2 to 14 carbon atoms and containing at least one heteroatom, preferably 1 to 3 heteroatoms, such as a nitrogen atom, an oxygen atom, and a sulfur atom. Specific examples thereof include 2-pyridyloxy, 2-pyrazyloxy, 2-pyrimidyloxy, 2-quinolyloxy, etc.

Examples of the aralkylthio group as the substituent include an aralkylthio group of 7 to 12 carbon atoms and specific examples thereof include benzylthio, 2-phenethylthio, etc.

Examples of the heteroarylthio group include a heteroarylthio group having 2 to 14 carbon atoms and containing at least one heteroatom, preferably 1 to 3 heteroatoms, such as a nitrogen atom, an oxygen atom and a sulfur atom. Specific examples thereof include 2-pyridylthio, 4-pyridylthio, 2-benzimidazolylthio, 2-benzoxazolylthio, 2-benzthiazolylthio, etc.

Examples of the substituted amino group include a group derived from an amino group by replacing one or two hydrogen atoms with a substituent such as an alkyl group, an aryl group and an aralkyl group.

Examples of the amino group substituted with an alkyl group, i.e., the alkyl-substituted amino group include a mono- or dialkylamino group such as N-methylamino, N,N-dimethylamino, N,N-diethylamino, N,N-diisopropylamino, N-cyclohexylamino, etc.

Examples of the amino group substituted with an aryl group, i.e., the aryl-substituted amino group include a mono- or diarylamino group such as N-phenylamino, N,N-diphenylamino, N,N-ditolylamino, N-naphthylamino, N-naphthyl-N-phenylamino, etc.

Examples of the amino group substituted with an aralkyl group, i.e., the aralkyl-substituted amino group include a mono- or diaralkylamino group such as N-benzylamino, N,N-dibenzylamino, etc.

One or more hydrogen atoms of the above substituents may be replaced with a halogen atom. Examples of the halogen atom include a fluorine atom, a chlorine atom, a bromine atom, an iodine atom, etc.

In the formula (I), at least one of $R^1$, $R^2$, $R^3$ and $R^4$ contains an alkenyl group, an alkadiene group, an alkatriene group or an epoxy group.

Examples of such a group containing an epoxy group include an epoxy group, a glycidyl group, etc., and preferred is a glycidyl group in view of reactivity.

Examples of the alkenyl group, the alkadiene group and the alkatriene group are the same as those listed above for $R^1$, $R^2$, $R^3$ and $R^4$.

$R^1$, $R^2$, $R^3$ and $R^4$ may bind to each other to form a ring. The ring is, for example, a 3- to 10-membered, preferably 5- or 6-membered, monocyclic ring or a polycyclic ring and may contain a heteroatom such as a nitrogen atom, an oxygen atom and a sulfur atom. Any two of, or three or more of $R^1$, $R^2$, $R^3$ and $R^4$ may bind to each other to form a ring. Examples of the ring include methylcyclopentyl, cyclohexyl, furyl, thienyl, pyrrolyl, pyridyl, etc.

Preferably, $R^1$ is an epoxy group, a glycidyl group, or an alkenyl group of 2 to 10 carbon atoms. This is because an epoxy group, a glycidyl group and an alkenyl group of 2 to 10 carbon atoms are highly reactive and therefore exhibit excellent antistatic performance when mixed with an embedding medium.

Examples of the alkenyl group of 2 to 10 carbon atoms represented by $R^1$ include vinyl, 1-propenyl, allyl, 1-butenyl, 2-butenyl, 3-butenyl, pentenyl, hexenyl, isopropenyl, 2-methyl-2-propenyl, 1-methyl-2-propenyl, 2-methyl-1-propenyl, etc.

Particularly preferably, $R^1$ is a glycidyl group or an alkenyl group of 1 to 6 carbon atoms in view of reactivity.

Preferably, $R^2$, $R^3$ and $R^4$ are independently an alkyl group of 1 to 6 carbon atoms, more preferably an alkyl group of 1 to 4 carbon atoms, particularly preferably a methyl group or an ethyl group. When $R^2$, $R^3$ and $R^4$ are the above groups, steric hindrance on $R^1$ can be prevented and sufficient reactivity can be obtained.

Preferably, the quaternary ammonium compound is a monomer, an oligomer or a mixture thereof. Examples of the quaternary ammonium compound as an oligomer include a quaternary ammonium compound in a dimer or trimer form or in the form of an oligomer with a molecular weight of about 1000 or less. Examples of the quaternary ammonium compound as a mixture of an oligomer with an oligomer or a monomer include an oligomer formed by the bonding between the alkenyl, the alkadiene, the alkatriene and/or the epoxy groups of quaternary ammonium compounds.

Preferably, the quaternary ammonium compound based on the formula (I) is glycidyl trimethylammonium, ethyl glycidyl dimethylammonium, diethyl glycidyl methylammonium, or triethyl glycidyl ammonium, and is particularly preferably glycidyl trimethylammonium.

Anion

The anion of the ionic liquid of the present invention is not particularly limited as long as it is a conjugate Lewis base constituting the ionic liquid. The anion is preferably $BF_4^-$, $PF_6^-$, $(CF_3SO_2)_2N^-$, a halide ion, a conjugate base of carboxylic acid, a conjugate base of sulfonic acid or a conjugate base of an inorganic acid. Among them, more preferred are $BF_4^-$, $PF_6^-$, and $(CF_3SO_2)_2N^-$, and particularly preferred is $(CF_3SO_2)_2N^-$ because of their low melting points and high heat resistance.

The anion may be commercial product or produced by a known method or a method similar to a known method.

Ionic Liquid

The ionic liquid used in the present invention is not particularly limited as long as it is a mixture of the above cation and anion. Preferably, the ionic liquid is glycidyl trimethylammonium bis(trifluoromethanesulfonyl)imide, ethyl glycidyl dimethylammonium bis(trifluoromethanesulfonyl)imide, diethyl glycidyl methylammonium bis(trifluoromethanesulfonyl)imide, or triethyl glycidyl ammonium bis(trifluoromethanesulfonyl)imide, and is particularly preferably glycidyl trimethylammonium bis(trifluoromethanesulfonyl)imide.

The ionic liquid is produced by a known method, for example, by mixing the anion and the cation.

The amount of the ionic liquid used is 1 to 50 vol %, preferably 5 to 35 vol %, more preferably 7.5 to 25 vol %, and particularly preferably 10 to 20 vol %, relative to the total volume of the composition.

Embedding Medium

The embedding medium used in the present invention comprises an epoxy-based resin, a methacrylate resin, or an unsaturated polyester resin. For the preparation of the embedding medium of the present invention, already polymerized epoxy-based resin, methacrylate resin, or unsaturated polyester resin may be used. Alternatively, the epoxy-based resin, methacrylate resin, or unsaturated polyester resin before polymerization may be used.

In view of strength, embedding performance and sectioning quality of the embedding medium of the present invention, the embedding medium preferably comprises an epoxy-based resin.

The amount of the epoxy-based resin, methacrylate resin, or unsaturated polyester resin used is 50 to 99 vol %, preferably 65 to 95 vol %, more preferably 75 to 92.5 vol %, particularly preferably 80 to 90 vol %, relative to the total volume of the composition.

Epoxy-Based Resin

The epoxy-based resin can be prepared by, for example, mixing a monomer with a polymerization initiator, a curing agent, and/or the like.

The monomer used to form the epoxy-based resin is not particularly limited and may be an aliphatic epoxy monomer or an aromatic epoxy monomer. The monomer may be one kind or a mixture of two or more kinds.

Examples of the aliphatic epoxy monomer include 3,4-epoxycyclohexylmethyl carboxylate, 3,4-epoxy-6-methylcyclohexylmethyl carboxylate, dimer acid glycidyl ester, hexahydrophthalic acid glycidyl ester, diglycidyl ether, butanediol diglycidyl ether, hexahydrobisphenol A diglycidyl ether, polyethylene glycol diglycidyl ether, polypropylene glycol diglycidyl ether, neopentyl glycol diglycidyl ether, trimethylolpropane triglycidyl ether, glycerol triglycidyl ether, pentaerythritol triglycidyl ether, triglycidyl isocyanurate, tetraglycidyl-1,3-bisaminomethylhexane, dipentaerythritol hexaglycidyl ether, etc.

Examples of the aromatic monomer include a bisphenol A epoxy monomer, a bisphenol F epoxy monomer, a bisphenol AD epoxy monomer, a bisphenol S epoxy monomer, a novolac epoxy monomer, a biphenyl epoxy monomer, a glycidyl ether epoxy monomer, a glycidyl amine epoxy monomer, etc.

The monomer used to form the epoxy-based resin may be a commercial product or produced by a known method. Examples of the commercial product of the monomer used to form the epoxy-based resin include Araldite CY-212, Epon 812, Epok 812 (all produced by ABBA company), etc.

Methacrylate Resin

The methacrylate resin can be prepared by, for example, mixing a monomer with a polymerization initiator, a curing agent, and/or the like.

The monomer used to form the methacrylate resin is not particularly limited but is preferably a mixture of a methacrylic acid ester, such as methyl methacrylate and butyl methacrylate, with a styrene monomer.

Unsaturated Polyester Resin

The polyester resin can be prepared by, for example, mixing a monomer with a polymerization initiator, a curing agent, and/or the like.

The monomer used to form the unsaturated polyester resin is not particularly limited but is preferably a mixture of Rigolac (trade name) with a styrene monomer.

Curing Agent

The embedding medium comprising an epoxy resin used in the present invention preferably comprises a curing agent. The curing agent is not particularly limited and examples thereof include carboxylic acid anhydrides, amines, sulfur-containing compounds, dicyandiamides, organic hydrazides, etc. The curing agent may be one kind or a mixture of two or more kinds.

The carboxylic acid anhydride is an anhydride of a carboxylic acid containing two or more carboxyl groups and is preferably an anhydride of a carboxylic acid containing two carboxyl groups. The carboxylic acid anhydride may be an aliphatic carboxylic anhydride, a cyclic aliphatic carboxylic anhydride, or an aromatic carboxylic anhydride.

Examples of the aliphatic carboxylic anhydride include acetic anhydride, maleic anhydride, propionic anhydride, succinic anhydride, acetylsuccinic anhydride, 3-dodecenyl succinic anhydride (DDSA), adipic anhydride, azelaic anhydride, citramalic anhydride, malonic anhydride, glutaric anhydride, citric anhydride, tartaric anhydride, oxoglutaric anhydride, pimelic anhydride, sebacic anhydride, itaconic anhydride, suberic anhydride, diglycol anhydride, etc.

Examples of the cyclic aliphatic carboxylic anhydride include hexahydrophthalic anhydride, cyclobutanedicarboxylic anhydride, cyclopentanedicarboxylic anhydride, norbornanedicarboxylic anhydride, hexahydrotrimellitic anhydride, tetrahydrophthalic anhydride, methyltetrahydrophthalic anhydride, tetrahydrophthalic anhydride, methyl endo-methylenetetrahydrophthalic anhydride, chlorendic anhydride, methylhexahydro nadic anhydride, etc.

Examples of the aromatic carboxylic anhydride include phthalic anhydride, trimellitic anhydride, pyromellitic anhydride, mellophanic anhydride, naphthalic anhydride, etc.

Any of the hydrogen atoms or hydrocarbon groups of the above carboxylic anhydrides may be replaced or substituted with a substituent.

Examples of the amines include diethylenetriamine, triethylenetetramine, diethylamino propylamine, N-aminoethyl piperazine, bis(4-amino-3-methylcyclohexyl)methane, m-xylylenediamine, menthanediamine, 3,9-bis(3-aminopropyl)-2,4,8,10-tetraoxaspiro[5.5]undecane, etc.

Examples of the sulfur-containing compounds include polysulfides, polymercaptans, etc.

Examples of the dicyandiamides include DICY-7 made by Yuka Shell Epoxy K.K., etc.

Examples of the organic hydrazides include adipic acid hydrazide, phthalic acid hydrazide, 7,11-octadecadiene-1,18-carbohydrazide, bisphenol A ether dicarboxylic acid hydrazide, etc.

The amount of the curing agent used is preferably 5 to 80 phr (parts per hundred parts of resin) relative to the embedding medium comprising an epoxy-based resin.

Optional Components

To the embedding medium of the present invention may be added a reaction accelerator, a polymerization initiator, a color pigment, a filler, a fiber, various additives, a solvent, a reactive diluent, etc. in an amount so as not to impair the effects of the invention.

Reaction Accelerator

The embedding medium comprising an epoxy resin used in the present invention preferably comprises a reaction accelerator, for example, tertiary amines such as triethylenediamine, benzyldimethylamine (BDMA), 2-(dimethylaminomethyl)phenol (DMP-10) and 2,4,6-tris(dimethylaminomethylphenol) (DMP-30); triphenylphosphine, etc.

Polymerization Initiator

The embedding medium comprising a methacrylate resin or an unsaturated polyester resin of the present invention preferably comprises a polymerization initiator. The polymerization initiator is not particularly limited and may be a thermal polymerization initiator or a photo polymerization initiator.

Examples of the photo polymerization initiator include radical reaction initiators such as an alkylphenone-based radical initiator, an acylphosphine oxide-based radical initiator and a titanocene-based radical initiator.

Examples of the thermal polymerization initiator include radical reaction initiators such as benzoyl peroxide (BPO) and azobisisobutyronitrile (AIBN).

The embedding medium comprising an epoxy resin of the present invention preferably comprises a polymerization initiator. The polymerization initiator is not particularly limited and may be a photo polymerization initiator.

Examples of the photo polymerization initiator include cationic polymerization initiators, for example, a salt containing a cation such as diazonium, sulfonium, iodonium and oxonium and an anion such as $PF_6^-$, $SbF_6^-$, $(C_6F_5)_4B^-$ and $BF_4^-$; etc.

The amount of the polymerization initiator used is preferably 0.1 to 10 phr (parts per hundred parts of resin) relative to the embedding medium comprising an epoxy-based resin, a methacrylate resin or an unsaturated polyester resin.

Preparation of Composition

The embedding resin composition for electron microscopy of the present invention can be obtained by mixing the ionic liquid with the embedding medium comprising an epoxy-based resin, a methacrylate resin or an unsaturated polyester resin.

The term "embedding resin composition for electron microscopy" herein refers to a liquid, paste or slurry composition used for embedding. Preferably, the embedding resin composition for electron microscopy is a composition before curing.

Preferably, the embedding resin composition for electron microscopy of the present invention is prepared by mixing the ionic liquid with the embedding medium comprising an epoxy-based resin, a methacrylate resin or an unsaturated polyester resin and, after embedding of a sample in the composition, polymerization and curing are performed. Polymerization in the composition can be performed by, for example, exposing the composition to light or heating the composition at 40 to 80° C. for 24 to 96 hours. Curing of the composition can be performed by, for example, heating the composition at normal temperature to 100° C. for 24 to 96 hours.

Performance of Composition

Antistatic Performance

The embedding resin composition for electron microscopy of the present invention has antistatic performance. The embedding resin composition for electron microscopy of the present invention has antistatic performance and can therefore prevent charging of a sample surface, thereby allowing detailed observations of the sample. In this way, sufficient resolution can be achieved.

The antistatic performance of the embedding resin composition for electron microscopy of the present invention is, when expressed in terms of the surface resistance of the composition, $1.0 \times 10^{15}$ Ω/sq or less, preferably $1.0 \times 10^{14}$ Ω/sq or less, particularly preferably $7.5 \times 10^{13}$ Ω/sq or less. When the surface resistance is in the above range, a sample surface can be efficiently prevented from being charged, thereby allowing detailed observations of various non-conductive samples. In addition to this, sufficient resolution can be achieved.

Preferably, the antistatic performance is such that, when a sample is photographed with a scanning electron microscope, no influence by charging is observed on the image, i.e., no image defect or distortion is observed.

Performance as Embedding Resin Composition

The embedding resin composition for electron microscopy of the present invention satisfies performance generally required of embedding resin compositions, including sectioning quality and embedding performance.

The term "embedding performance" herein refers to the ability of, when a sample is photographed with an electron microscope, providing an image with sufficient quality. The term "sectioning quality" herein refers to the ability of providing sufficiently thin sections of an embedded sample.

Use

The embedding resin composition for electron microscopy of the present invention can be used for embedding of a sample to be observed with an electron microscope.

The sample to be embedded is not particularly limited as long as it can be subjected to the embedding step described later, and the sample may be a biological sample or a non-biological sample.

Biological Samples

Preferably, the biological sample is a cell or tissue of an animal or plant.

Examples of the plant include procaryotes, protists, fungi, algae, terrestrial plants, etc.

Examples of the procaryotes include bacteria such as *Escherichia coli*, lactic acid bacteria, *Streptococcus pneumoniae*, nitrite bacteria, nitrate bacteria, and sulfur bacteria; cyanobacteria such as green sulfur bacteria, purple sulfur bacteria, *Oscillatoria*, and *Nostoc*; etc.

Examples of the protists include protozoa, unicellular algae, etc. Examples of the protozoa include Rhizopoda such as amoebas; Ciliophora such as *Paramecium*; Mastigophora such as *Trypanosoma*; Sporozoa such as malaria pathogens; etc. Examples of the unicellular algae include Euglenida such as *Euglena* and *Trachelomonas*; Dinoflagellata such as *Ceratium* and *Noctiluca*; Bacillariophyceae such as *Pinnularia* and *Navicula*; etc.

Examples of the fungi include Myxomycota, Eumycota, etc. Examples of the Myxomycota include Myxomycetes such as *Stemonitis* and *Trichia*; cellular slime molds such as

*Dictyostelium* and *Acrasis*; etc. Examples of the Eumycota include Oomycota such as *Saprolegnia, Achlya,* and *Pythium*; Zygomycetes such as *Rhizopus, Mucor,* and Zoopagales; Ascomycetes such as *Aspergillus, Penicillium, Neurospora, Peziza,* and yeasts; Basidiomycetes such as *Tricholoma matsutake, Lentinula, Auricularia,* and *Flammulina*; etc.

Examples of the algae include Red algae such as layer, agar-agar, *Gloiopeltis, Meristotheca,* and *Batrachospermum*; Brown algae such as kelp, wakame, *Hizikia, Nemacystus, Sargassum,* and *Padina*; Green algae such as volvox, *Chlamydomonas,* chlorella, sea lettuce, and *Acetabularia*; stoneworts such as *Chara* and *Nitella*; etc.

Examples of the terrestrial plants include moss plants such as *Marchantia, Conocephalum, Polytrichum,* and *Sphagnum*; fern plants such as whisk fern, clubmoss, common horsetail, scouring rush, bracken, and Japanese royal fern; gymnosperms such as cycads, ginkgo, Japanese red pine, Japanese cedar, and Japanese cypress; angiosperms such as rice plant, palm tree, and orchid; etc.

Examples of the animal include Porifera, Coelenterate, Platyhelminthes, Aschelminthes, Annelida, Mollusca, Arthropoda, Chaetognatha, Echinodermata, Vertebrata, etc.

Examples of the Porifera include *Halichondria okadai, Haliclona, Euplectella,* etc. Examples of the Coelenterate include sea anemones, corals, hydras, etc. Examples of the Platyhelminthes include planarians, tapeworms, *Bipalium,* etc. Examples of the Aschelminthes include Nemathelminthes such as nematodes, roundworms, pinworms, and hairworms; Trochelminthes such as *Brachionus, Trichocerca,* and *Rotaria*; etc.

Examples of the Annelida include earthworms, *Tubifex, Neanthes,* feather duster worms, leeches, etc. Examples of the Mollusca include pelecypods such as common orient clams and *Corbicula*; gastropods such as horned turban shell and land snails; cephalopods such as octopuses and squids; etc. Examples of the Arthropoda include crustaceans such as water fleas, shrimps, and crabs; centipedes such as scolopendromorph centipede and *Thereuonema tuberculata*; spiders such as *Nephila clavata* and mites; insects such as grasshoppers and beetles; etc. Examples of the Chaetognatha include *Flaccisagitta hexaptera* etc. Examples of the Echinodermata include sea lilies, feather stars, sea cucumbers, sea urchins, star fishes, etc.

Examples of the Vertebrata include Protochordata such as sea squirts, Doliolida, and lancelets; Agnatha such as lampreys; cartilaginous fishes such as sharks and rays; bony fishes such as carp and Pacific saury; amphibians such as frogs and newts; reptiles such as lizards, turtles, and snakes; birds such as pigeons, swallows, pheasants, sparrows, and chickens; mammals such as human, monkeys, lions, whales, rats, cattles, horses, and sheeps; etc.

Examples of the biological sample include a cell or tissue of an animal or plant.

Examples of the cell or tissue of an animal include epithelial tissue such as the epidermis of the skin, hair, nail, the inner wall of the digestive tract, blood capillaries, and salivary gland; connective tissue such as the dermis of the skin, tendon, blood, cartilage, bone, and fat; muscular tissue such as striated muscle, smooth muscle, and cardiac muscle; nervous tissue such as neurons; etc. and the cells of these tissues.

The examples of the cell or tissue of an animal further include the cells or tissue of organs, for example, digestive system organs such as oral cavity, salivary gland, esophagus, stomach, pancreas, gallbladder, liver, duodenum, small intestine, large intestine, appendix vermiformis, and rectum; circulatory system organs such as heart, aorta, inferior vena cava, brachial artery, brachial vein, carotid artery, jugular vein, subclavian artery, and subclavian vein; respiratory system organs such as trachea, bronchus, and lung; excretory system organs such as kidney, ureter, and urinary bladder; nervous system organs such as brain, spinal cord, and peripheral nerves; skeletal system organs such as cranial bone, vertebral column, pelvis, thigh bone, and shoulder blade; muscular system organs such as greater pectoral muscle, biceps brachii muscle, and frontal muscle; genital system organs such as gonad, oviduct, vas deferens, womb, and placenta; endocrine system organs such as pituitary gland, thyroid gland, parathyroid gland, adrenal gland, pancreas, and gonad; sensory system organs such as eye, ear, nose, tongue, and skin; etc.

Examples of the cell or tissue of a plant include epidermal tissue, mechanical tissue, absorptive tissue, assimilation tissue, conductive tissue, storage tissue, aerenchyma, secretory tissue, etc. and the cells of these tissues.

The examples of the cell or tissue of a plant further include the cells or tissue of organs, for example, root, stem, leaves, seed, flower, etc.

Non-Biological Sample

The non-biological sample may be an organic substance or an inorganic substance. The non-biological sample may be a naturally occurring sample or an artificially synthesized sample. Examples of the non-biological sample include resins, rubbers, synthetic resins, pigments, coating materials, cosmetics, pharmaceutical drugs, ceramics, magnetic bodies, magnetic materials, semiconductors, metals, metal oxides, minerals, organic salts, inorganic salts, etc.

After a sample is harvested, the sample may be directly subjected to embedding or first dehydrated and then subjected to embedding. The sample to be embedded may be a sample containing water.

The size of the sample is not particularly limited and the sample may be a powder. Examples of the powder sample include foods such as wheat flour, coffee, salt, sugar, starch, spices and seasonings; pharmaceutical drugs such as granules, cosmetics and powdered medicine; metal oxides such as alumina, iron oxide and tin oxide; metals, feeds, detergents, cosmetics, pigments, powdered paints, carbon toners, magnetic bodies, magnetic materials, cements, glass, abrasives, sand, semiconductors, ceramics, minerals, sintered bodies, gunpowders, etc.

Method for Observing Sample with Electron Microscope

Embedding Step

The method for observing a sample with an electron microscope of the present invention comprises the step of embedding a sample in the above embedding resin composition for electron microscopy.

The embedding step can be performed in accordance with a known method or a method similar to a known method except that the above composition is used. The embedding step comprises, for example, embedding a sample to be observed in the embedding resin composition for electron microscopy of the present invention. In this step, the sample to be observed may be a non-conductive sample such as a biological sample, a non-biological sample, a powder sample, etc. When a sample containing water is used, the sample may be, for example, dehydrated in an ascending series of alcohol, acetone, etc. and then embedded in the resin composition. When a sample not containing water, for example, a non-biological sample or a powder sample is used, the sample may be directly embedded in the resin composition or mixed with the resin composition so as to be embedded therein. When a biological sample is used, the sample may be, for example, first fixed in glutaraldehyde etc. and then a part to be observed is cut out and subjected to embedding.

According to the method of the present invention, since the embedding resin composition for electron microscopy has antistatic performance, the surface structure of a sample can be sufficiently observed. Further, since the embedding resin composition for electron microscopy exhibits satisfactory performance as an embedding resin composition, the embedding resin composition can be used for embedding of various samples.

Non-Stained Sample

The method for observing a sample with an electron microscope of the present invention can be used for observation of anon-stained sample. Anon-stained sample can provide image contrast which represents the elemental composition of the sample itself.

Staining Step

The method for observing a sample with an electron microscope of the present invention can comprise the step of staining a sample. The staining step enables detailed observations of the surface structure or internal structure of the sample. The staining step can be performed on both biological samples and non-biological samples.

Staining can be performed by a known method. For example, the following methods can be employed:
1) en bloc staining: Osmic acid staining alone, tannic acid-osmic acid staining (TaO method), or potassium ferrocyanide-osmic acid-thiocarbohydrazide-osmic acid multistaining (OTO method) is performed and subsequently additional staining, such as uranyl acetate staining, lead staining (Walton method), phosphotungstic acid staining, and potassium permanganate staining, is performed; or
2) after preparation of the sample surface to be observed, direct staining of a sample surface with uranyl acetate solution is performed.

The staining step may be performed before or after the embedding step, but is preferably performed before the embedding step. This is because staining of a sample before embedding provides satisfactory staining results regardless of the resin used.

Preparation Step of Surface to be Observed

The method for observing of a sample with an electron microscope of the present invention preferably further comprises the step of thin sectioning a sample or exposing the surface of a sample. The thin sectioning step can be performed using a known device such as an ultramicrotome and a polishing machine. In the thin sectioning step, a sample is preferably thin sectioned into 50 to 100 nm thick slices. Exposure of the surface can be achieved by means of an ultramicrotome with a diamond knife, a focused ion beam (FIB) apparatus, an ion polishing machine, or a precision polishing machine, and the obtained surface can be observed with a scanning electron microscope.

The electron microscope used for the observation method of the present invention is not particularly limited and may be any of a transmission electron microscope (TEM), a scanning electron microscope (SEM) and a scanning transmission electron microscope (STEM). For the observation of a sample surface, preferred are a SEM and a SEM having a built-in FIB apparatus.

EXAMPLES

The present invention will be illustrated below with reference to Examples, but the present invention is not limited thereto.

For observations of the surface of embedded biological samples, a scanning electron microscope ("S-800" produced by Hitachi High-Technologies Corporation) was used. For observations of the surface of embedded non-biological samples, a SEM having a built-in FIB apparatus ("Quanta FEG (FEI)" produced by Japan FEI Company) was used.

For thin sectioning, a microtome ("UltracutE" produced by Reichert AG (current Leica Microsystems GmbH)) was used.

The unspecified reagents used below are all commercial products.

Evaluation Method

Polymerizability was determined to be excellent in cases where polymerization of a composition occurred.

Sectioning quality was determined to be excellent in cases where a sample embedded in a composition was successfully thin sectioned into 50 nm thick slices.

Embedding performance was determined to be excellent in cases where the quality of a photograph of a sample taken by a SEM (scanning electron microscope) was comparable with that of a photograph of the sample embedded in an embedding medium composition not containing the ionic liquid described later.

Antistatic performance in the observation of a biological sample was determined to be excellent in cases where the surface resistance was $1.0 \times 10^{15}$ or less. Antistatic performance in the observation of a non-biological sample was determined to be excellent in cases where a photograph of the sample taken by a scanning electron microscope showed no influence by charging, i.e., no image defect or distortion.

Observation of Biological Sample (Examples 1 to 3 and Comparative Example 1)

Example 1

Preparation of Epoxy-Based Resin

An epoxy-based resin was prepared according to Luft's formulation (6:4). EPON 812 resin kit produced by TABB Laboratories Equipment Ltd was used. An amount of 4.7 ml of EPON 812 (produced by Shell Chemicals Co.) as an epoxy monomer was mixed with 2.8 ml of methyl nadic anhydride (MNA) and 2.5 ml of dodecenyl succinic anhydride (DDSA) as curing agents. To the resulting mixture, 0.15 ml of 2,4,6-tris(dimethylaminomethyl)phenol (DMP-30) as a polymerization accelerator was added to give an epoxy-based resin in a paste form.

Preparation of Embedding Resin Composition for Electron Microscopy

An amount of 4.00 ml of the above epoxy-based resin was mixed with 1.00 ml of N-glycidyl trimethylammonium bis(trifluoromethanesulfonyl)imide (produced by Japan Carlit Co., Ltd.; hereinafter also referred to as "GTA-TFSI") as an ionic liquid to give an embedding resin composition for electron microscopy in a paste form.

Embedding

Rat liver tissue was used as a sample to be observed. The liver tissue sample was fixed in 2% glutaraldehyde+2.5% formaldehyde solution. A cut out of the fixed sample was postfixed in 2% osmic acid/1% potassium ferrocyanide solution and en bloc staining was performed with 1% uranyl acetate aqueous solution.

The sample to be observed was mixed with the embedding resin composition and poured into a mold. The embedding resin composition was heated to a temperature range of 63 to 65° C. and this temperature was maintained for 48 hours so that the composition was polymerized and cured.

The cured embedding resin composition was cut and thin sectioned by means of the ultramicrotome with a diamond knife to produce a smooth surface on the embedding resin composition. Thus the embedding resin composition to be observed with the SEM was prepared. The composition was mounted on the sample stage of the SEM with silver paste, and without further treatment such as conductive coating, the smooth surface of the composition was observed with the SEM.

Example 2

An experiment was conducted in the same manner as in Example 1 except that the amount of the epoxy-based resin was 4.50 ml and that the amount of GTA-TFSI was 0.50 ml.

Example 3

An experiment was conducted in the same manner as in Example 1 except that the amount of the epoxy-based resin was 4.75 ml and that the amount of GTA-TFSI was 0.25 ml.

Comparative Example 1

An experiment was conducted in the same manner as in Example 1 except that the amount of the epoxy-based resin was 5.00 ml and that the amount of GTA-TFSI was 0 ml.

The results of Examples 1 to 3 and Comparative Example 1 are shown in Table 1.

An amount of 3.75 ml of the epoxy-based resin prepared in Example 1 was mixed with 1.25 ml of GTA-TFSI as an ionic liquid to give an embedding resin composition for electron microscopy in a paste form.

Embedding

A waste toner of a color copier was used as a sample to be observed. An amount of 5 parts by weight of the sample to be observed was mixed with 95 parts by weight of the embedding resin composition and poured into a mold. The embedding resin composition was heated to a temperature range of 63 to 65° C. and this temperature was maintained for 48 hours so that the composition was polymerized and cured.

Figure 3:
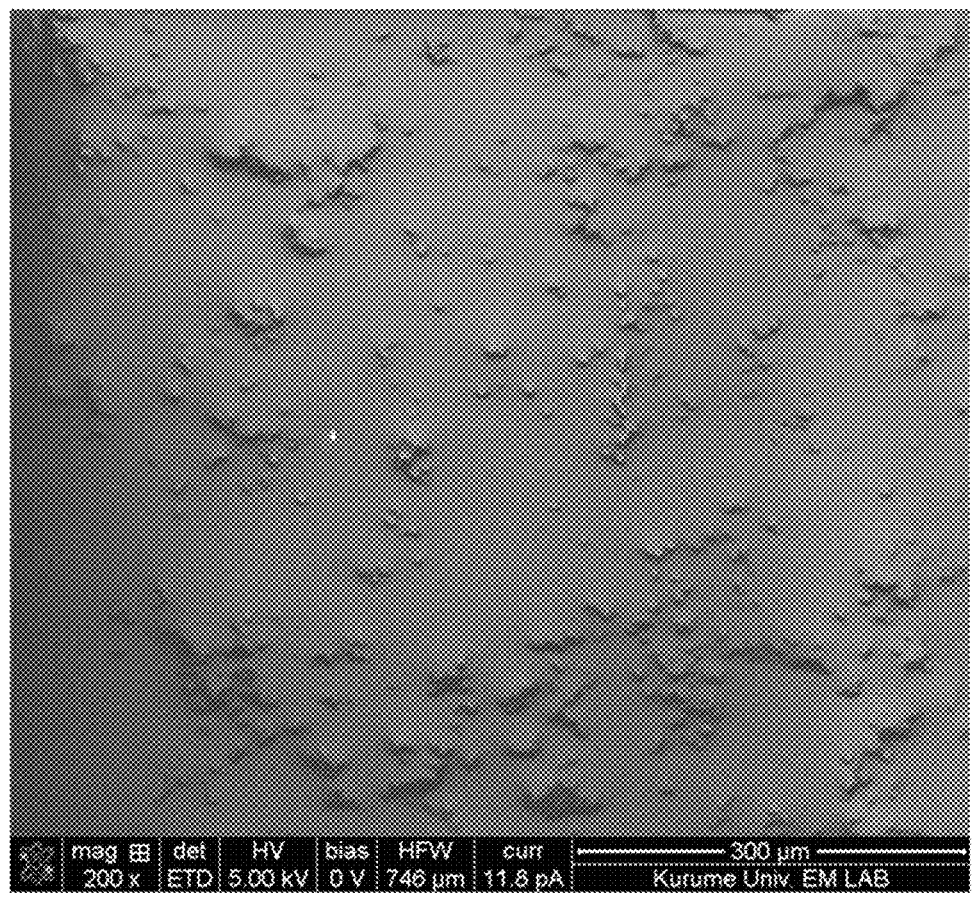
FIG. 3 is a photograph showing an electron microscope secondary electron image of a waste toner embedded in the embedding resin composition for electron microscopy of Example 4 (200-fold magnification).
Figure 4:
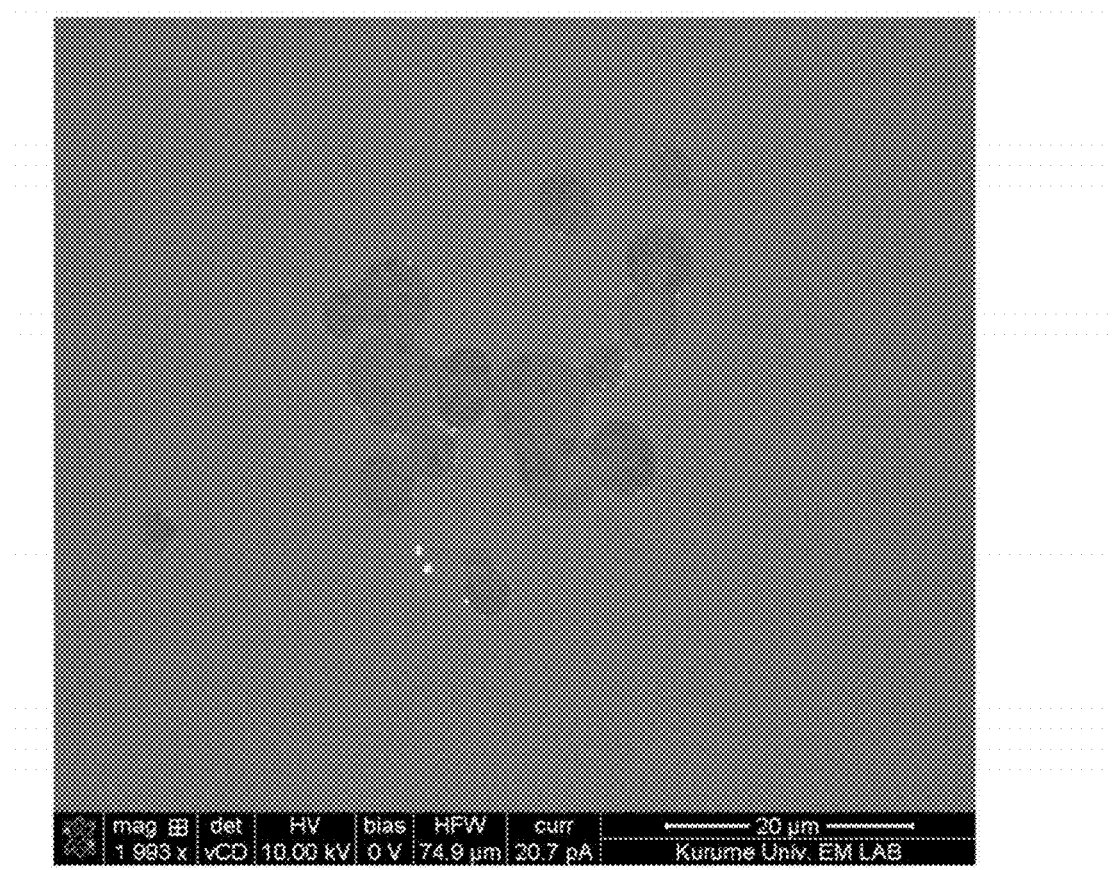
FIG. 4 is a photograph showing an electron microscope backscattered electron image of a waste toner embedded in the embedding resin composition for electron microscopy of Example 4 (2000-fold magnification).

The cured embedding resin composition was cut and thin sectioned by means of the ultramicrotome with a diamond knife to produce a smooth surface on the embedding resin composition. Thus the embedding resin composition to be observed with the SEM was prepared. The composition was mounted on the sample stage of the SEM with silver paste, and without further treatment such as conductive coating, the smooth surface of the composition was observed with the SEM. The obtained secondary electron image and backscattered electron image are shown in FIGS. 3 and 4, respectively.

Comparative Example 2

An experiment was conducted in the same manner as in Example 4 except that a resin composition consisting of 5.00

TABLE 1

| | Embedding resin composition | | | | Results | | | | |
| | Ionic liquid | | Epoxy-based resin | | | | | Antistatic performance | |
| | Amount added (ml) | Mixing ratio (%) | Amount added (ml) | Mixing ratio (%) | Polymerizability | Sectioning quality | Embedding performance | Surface resistance (Ω/sq) | Evaluation results |
|---|---|---|---|---|---|---|---|---|---|
| Example 1 | 1.00 | 20 | 4.00 | 80 | Good | Good | Good | $2.8 \times 10^{13}$ | Good |
| Example 2 | 0.50 | 10 | 4.50 | 90 | Good | Good | Good | $4.8 \times 10^{13}$ | Good |
| Example 3 | 0.25 | 5 | 4.75 | 95 | Good | Good | Good | $3.2 \times 10^{14}$ | Good |
| Comparative Example 1 | 0 | 0 | 5.00 | 100 | Good | Good | Good | $>10^{15}$ | Poor |

Evaluation Results

It was revealed that the embedding resin compositions of Examples 1 to 3 had sufficient antistatic performance, while maintaining basic performance required of an embedding resin composition, including sectioning quality and embedding performance.

FIG. 1 shows a SEM secondary electron image observed in Example 1. As shown in FIG. 1, no charging on the sample surface was observed and the shape of the sample surface could be sufficiently observed.

Figure 2:
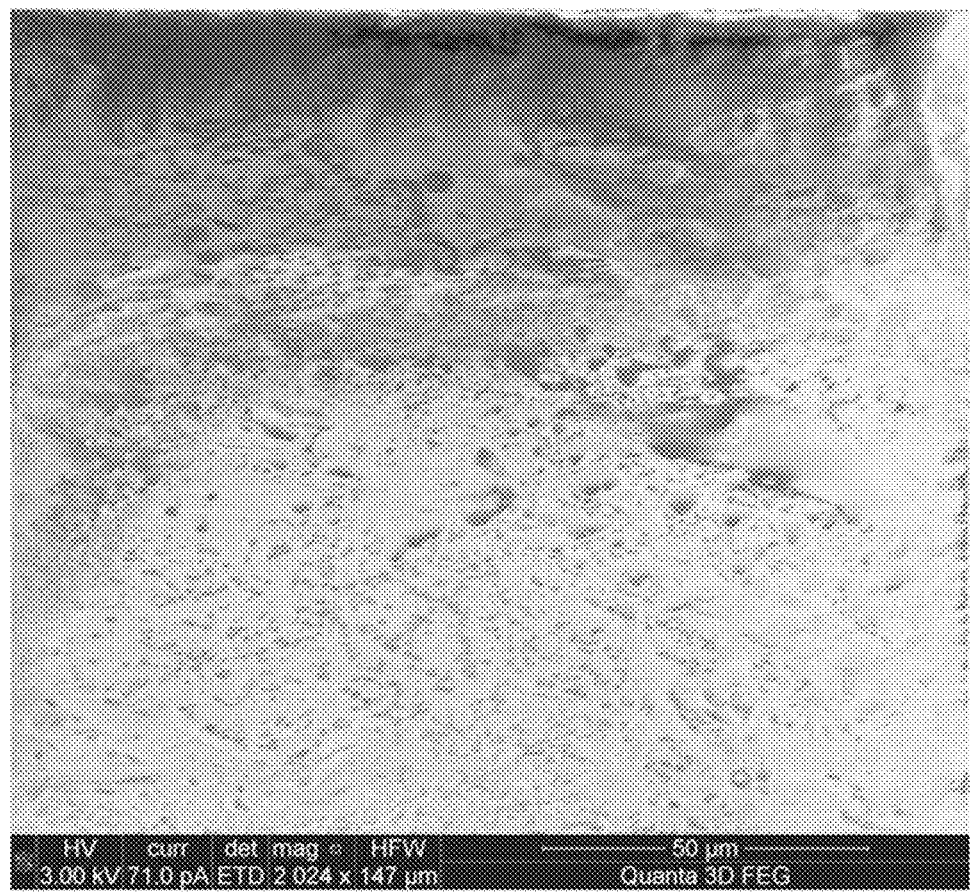
FIG. 2 is a photograph showing the results of electron microscope observation of hepatocytes embedded in the embedding resin composition for electron microscopy of Comparative Example 1 (2024-fold magnification).

FIG. 2 shows a SEM secondary electron image observed in Comparative Example 1. As shown in FIG. 2, charging on the sample surface was observed and the conditions of the surface could not be sufficiently observed.

Observation of Non-Biological Sample (Examples 4 and 5 and Comparative Examples 2 and 3)

Example 4

Figure 5:
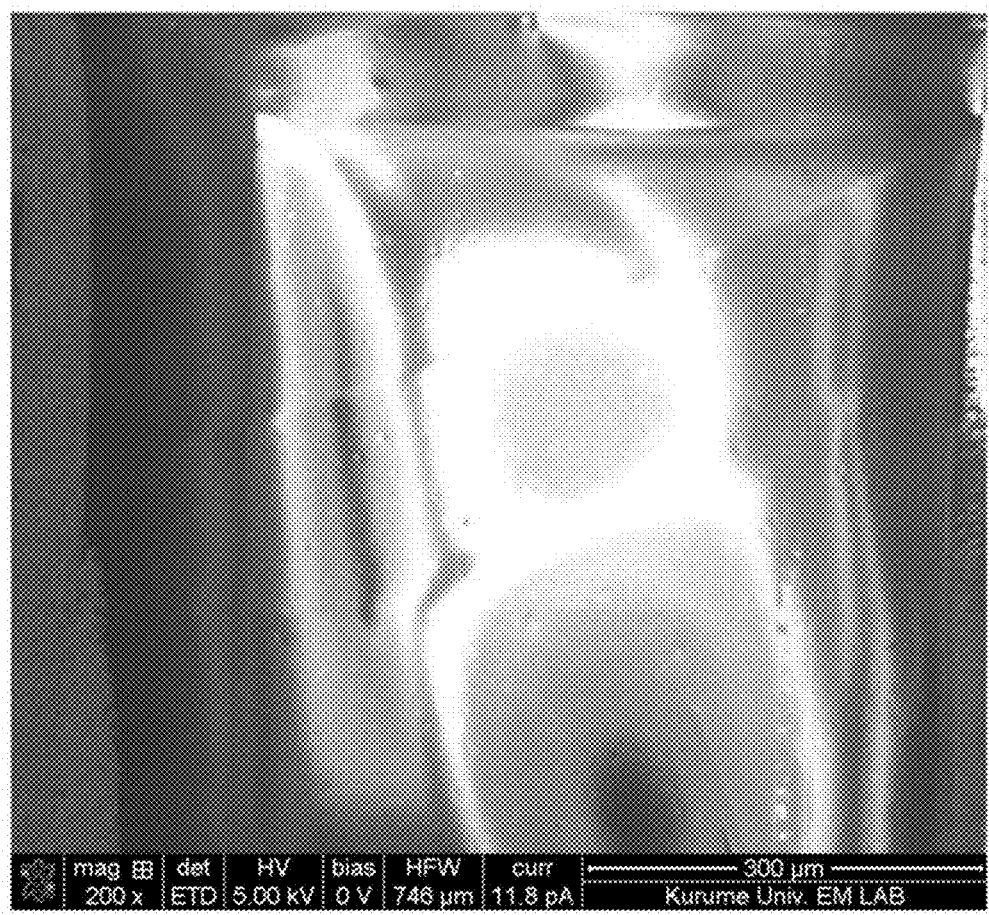
FIG. 5 is a photograph showing an electron microscope secondary electron image of a waste toner embedded in the embedding resin composition for electron microscopy of Comparative Example 2 (200-fold magnification).
Figure 6:
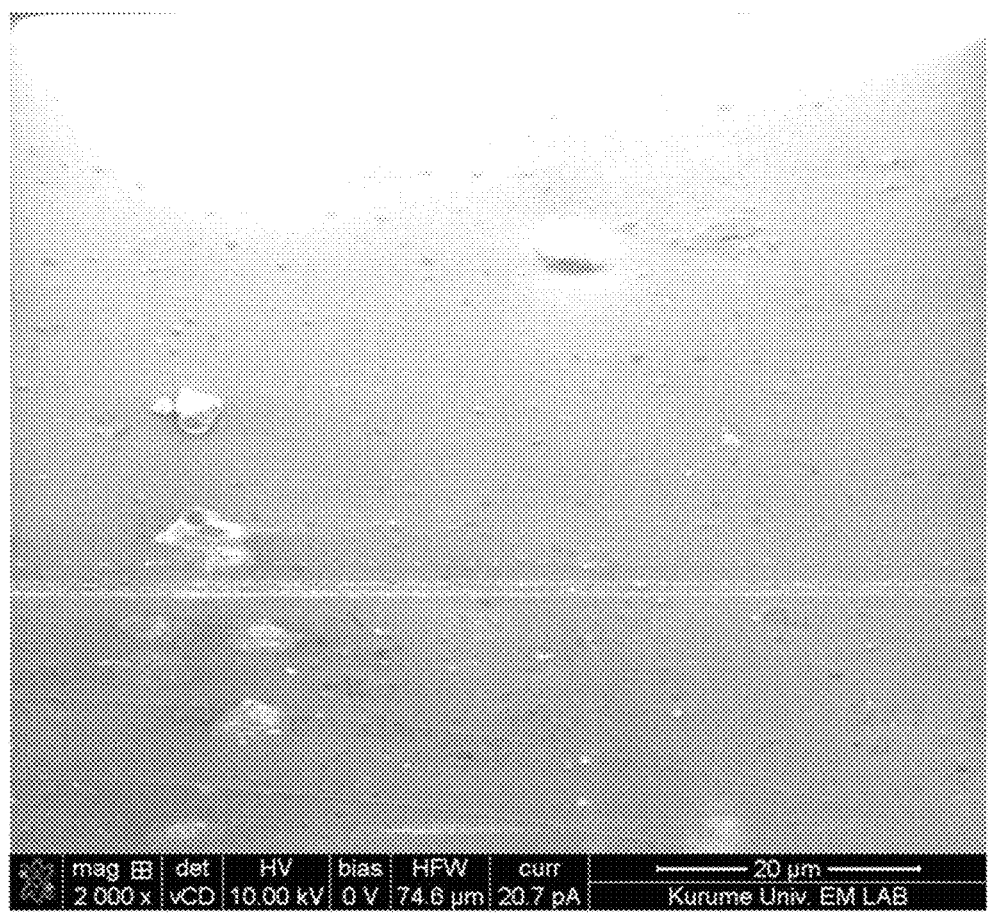
FIG. 6 is a photograph showing an electron microscope backscattered electron image of a waste toner embedded in the embedding resin composition for electron microscopy of Comparative Example 2 (2000-fold magnification).

Preparation of Embedding Resin Composition for Electron Microscopy ml of the epoxy-based resin and not containing the ionic liquid was used. The obtained secondary electron image and backscattered electron image are shown in FIGS. 5 and 6, respectively.

Example 5

Figure 7:
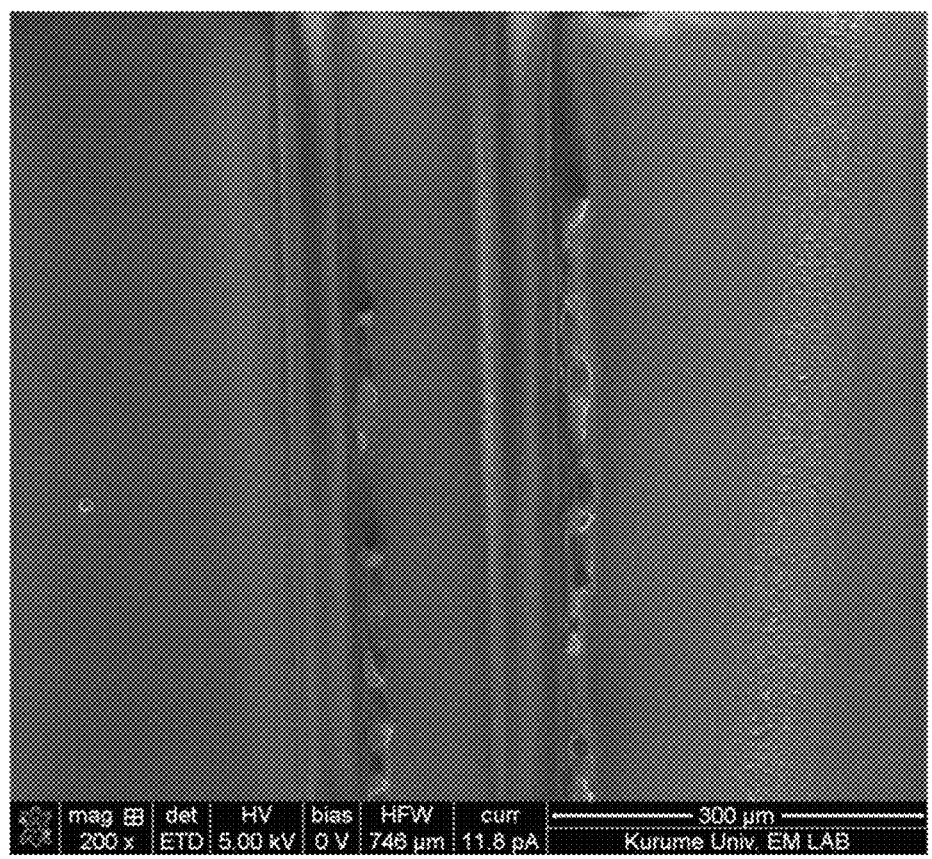
FIG. 7 is a photograph showing an electron microscope secondary electron image of a plastic sticky note embedded in the embedding resin composition for electron microscopy of Example 5 (200-fold magnification).
Figure 8:
FIG. 8 is a photograph showing an electron microscope backscattered electron image of a plastic sticky note embedded in the embedding resin composition for electron microscopy of Example 5 (1200-fold magnification).
Figure 9:
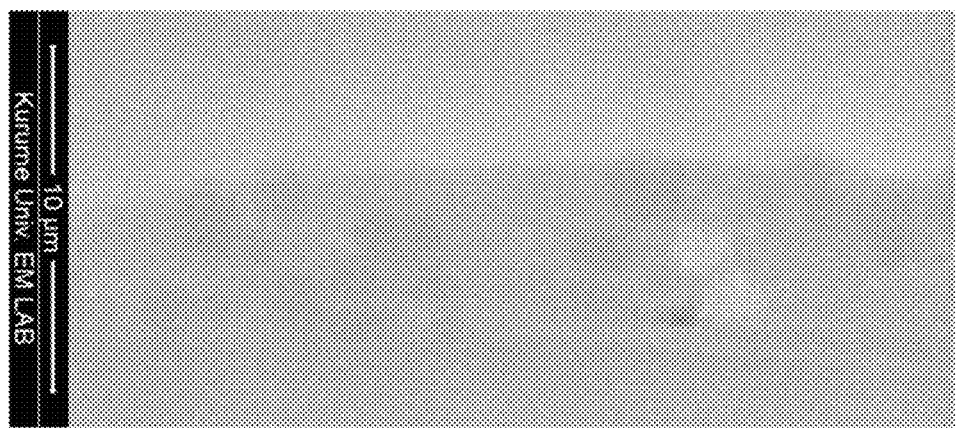
FIG. 9 is a photograph showing a backscattered electron image of the adhesive part of a plastic sticky note embedded in the embedding resin composition for electron microscopy of Example 5 (5000-fold magnification).

A plastic sticky note (with adhesive) was used as a sample to be observed. The embedding resin composition in a paste form prepared in Example 1 was poured into a mold and the sample to be observed was embedded. The embedding resin composition was heated at 63 to 65° C. for 48 hours so that the composition was polymerized and cured. The surface of the cured embedding resin composition was cut and thin sectioned by means of the ultramicrotome to produce a smooth surface on the embedding resin composition. Thus the embedding resin composition to be observed with the SEM was prepared. The composition was mounted on the sample stage of the SEM with silver paste, and without further treatment such as conductive coating, the smooth surface of the composition was observed with the SEM. The obtained secondary electron image and backscattered electron image are shown in FIGS. 7 and 8, respectively. The backscattered electron image of the adhesive part of the plastic sticky note is shown in FIG. 9.

Comparative Example 3

Figure 10:
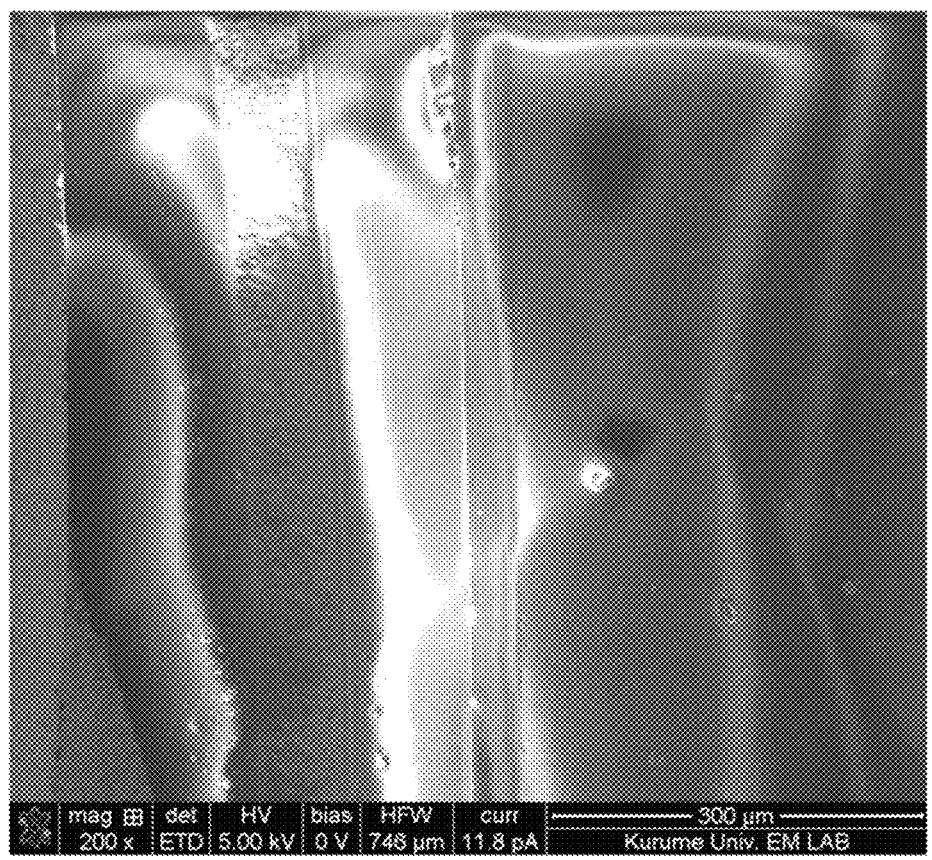
FIG. 10 is a photograph showing an electron microscope secondary electron image of a plastic sticky note embedded in the embedding resin composition for electron microscopy of Comparative Example 3 (200-fold magnification).
Figure 11:
FIG. 11 is a photograph showing an electron microscope backscattered electron image of a plastic sticky note embedded in the embedding resin composition for electron microscopy of Comparative Example 3 (1200-fold magnification).

An experiment was conducted in the same manner as in Example 5 except that a resin composition consisting of 5.00 ml of the epoxy-based resin and not containing the ionic liquid was used. The obtained secondary electron image and backscattered electron image are shown in FIGS. 10 and 11, respectively.

The results of Examples 4 and 5 and Comparative Examples 2 and 3 are shown in Table 2.

taining the ionic liquid, image defects and image distortion occurred and thus the shape of the plastic sticky note could not sufficiently be observed.

As shown in the backscattered electron image of Example 5 (see FIG. 8), when the embedding resin composition used was the mixture of the epoxy-based resin and the ionic liquid, no strong charging on the sample surface was observed and thus the compositional contrast of the sample could be obtained. The adhesive part of the sample could also be clearly observed (see FIG. 9). On the other hand, as shown in the backscattered electron image of Comparative Example 3 (see FIG. 11), strong noise due to strong charging was observed and thus the sample could not be sufficiently observed.

TABLE 2

| | Embedding resin composition | | | | | Results | | | |
|---|---|---|---|---|---|---|---|---|---|
| | Ionic liquid | | Epoxy-based resin | | | | | | |
| | Amount added (ml) | Mixing ratio (%) | Amount added (ml) | Mixing ratio (%) | Sample | Polymerizability | Sectioning quality | Embedding performance | Antistatic performance |
| Example 4 | 1.25 | 25 | 3.75 | 75 | Waste toner | Good | Good | Good | Good |
| Example 5 | 1.25 | 25 | 3.75 | 75 | Sticky note | Good | Good | Good | Good |
| Comparative Example 2 | 0 | 0 | 5 | 100 | Waste toner | Good | Good | Good | Poor |
| Comparative Example 3 | 0 | 0 | 5 | 100 | Sticky note | Good | Good | Good | Poor |

Evaluation Results

As is apparent from Table 2, the embedding resin compositions of Examples 4 to 5 had sufficient antistatic performance, while maintaining basic performance required of an embedding resin composition, including sectioning quality and embedding performance.

As shown in the secondary electron image of Example 4 (see FIG. 3), when the embedding resin composition used was the mixture of the epoxy-based resin and the ionic liquid, no charging on the sample surface was observed and the shape of the waste toner could be sufficiently observed. On the other hand, as shown in the secondary electron image of Comparative Example 2 (see FIG. 5), when the embedding resin composition used was the composition consisting of the epoxy-based resin and not containing the ionic liquid, image defects and image distortion occurred and thus the shape of the waste toner could not sufficiently be observed.

As shown in the backscattered electron image of Example 4 (see FIG. 4), clear compositional contrast of the toner could be obtained. On the other hand, as shown in the backscattered electron image of Comparative Example 2 (see FIG. 6), due to strong charging on the sample, a meaningful image could not be obtained and thus the compositional contrast of the sample was not obtained.

As shown in the secondary electron image of Example 5 (see FIG. 7), when the embedding resin composition used was the mixture of the epoxy-based resin and the ionic liquid, no charging on the sample surface was observed and the shape of the plastic sticky note could be sufficiently observed. On the other hand, as shown in the secondary electron image of Comparative Example 3 (see FIG. 10), when the embedding resin composition used was the composition consisting of the epoxy-based resin and not con- Example 6

Figure 12:
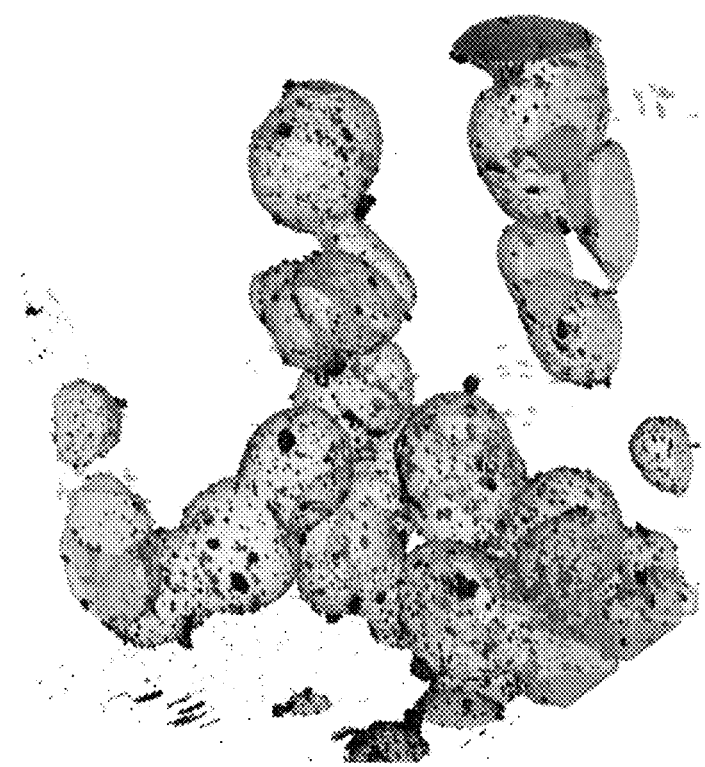
FIG. 12 is a photograph showing a three-dimensional reconstruction image of a waste toner in Example 6.

The embedded waste toner of a color copier in Example 4 was used as a sample to be observed. The sample surface was serially cut with FIB with a cutting thickness of 100 nm and the freshly cut smooth surface was observed with the SEM in the same manner as in Example 4. This cutting and observation cycle was repeated 377 times to produce successive images of the cut surface of the embedded sample (observation area: 42 μm×42 μm×38 μm, voxel size: 41.6 nm×41.6 nm×100 nm). The obtained images were processed with Avizo 6.3 software (VSG Inc., Bordeaux, France) to reconstruct a three-dimensional image and thus a three-dimensional image of the waste toner particles was obtained. The obtained image is shown in FIG. 12.

Evaluation Results

As shown in the three-dimensional reconstruction image of Example 6 (see FIG. 12), when the embedding resin composition used was the mixture of the epoxy-based resin and the ionic liquid, no influence due to charging was observed and thus the three-dimensional structure of the waste toner could be observed in detail.

INDUSTRIAL APPLICABILITY

The embedding resin composition for electron microscopy of the present invention comprising an ionic liquid and an embedding medium comprising an epoxy-based resin, a methacrylate resin or an unsaturated polyester resin has antistatic performance and is therefore industrially useful.

The invention claimed is:

1. A method for observing a sample with an electron microscope, the method comprising following steps of embedding a sample in the embedding resin composition having antistatic performance and comprising glycidyl trimethylammonium bis(trifluoromethanesulfonyl)imide and an embedding medium comprising an epoxy-based resin, a methacrylate resin or an unsaturated polyester resin,

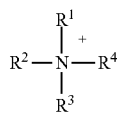
(I)

for electron microscopy, in order to observe a sample with an electron microscope, (i) preparation of the embedding resin composition comprising glycidyl trimethylammonium bis(trifluoromethanesulfonyl)imide for electron microscopy, by mixing glycidyl trimethylammonium bis(trifluoromethanesulfonyl)imide with the embedding medium, (ii) embedding of the sample in the embedding resin composition comprising glycidyl trimethylammonium bis(trifluoromethanesulfonyl)imide, (iii) polymerization and curing the embedded sample in the embedding resin composition comprising glycidyl trimethylammonium bis(trifluoromethanesulfonyl)imide.

2. The observation method according to claim 1, wherein the method comprises the step of staining a sample and the staining step is performed before the embedding step.

3. The observation method according to claim 1, wherein the electron microscope is a scanning electron microscope.

4. The observation method according to claim 1, wherein the sample is a biological sample.

5. The observation method according to claim 4, wherein the biological sample is a cell or tissue of a plant or animal.

6. The observation method according to claim 1, wherein the sample is a non-biological sample.

7. The observation method according to claim 6, wherein the non-biological sample is a resin, a rubber, a synthetic resin, a pigment, a coating material, a cosmetic, a pharmaceutical drug, a ceramic, a magnetic body, a magnetic material, a semiconductor, a metal, a metal oxide, a mineral, an organic salt, or an inorganic salt.

8. The observation method according to claim 1, wherein the sample is a powder.

9. The observation method according to claim 1, wherein an embedding medium comprising an epoxy-based resin or a methacrylate resin.

10. The observation method according to claim 1, wherein the amount of glycidyl trimethylammonium bis(trifluoromethanesulfonyl)imide is 5 to 35 vol % relative to the total volume of the composition.

11. The observation method according to claim 6, wherein the non-biological sample is a metal oxide or a ceramic.

* * * * *

UNITED STATES PATENT AND TRADEMARK OFFICE
CERTIFICATE OF CORRECTION

PATENT NO. : 9,870,894 B2
APPLICATION NO. : 14/342460
DATED : January 16, 2018
INVENTOR(S) : Keisuke Ohta et al.

It is certified that error appears in the above-identified patent and that said Letters Patent is hereby corrected as shown below:

On the Title Page

At item (54), Line 2, "MICROSCOPEY" should be -- MICROSCOPY --.

At Column 1, below Title, insert -- (71) Applicant: KURUME UNIVERSITY, Fukuoka (JP) --.

At Column 1, below Title, item "(75)" should be -- (72) --.

Signed and Sealed this
Fifth Day of June, 2018

Andrei Iancu
*Director of the United States Patent and Trademark Office*